United States Patent [19]
Laboureau

[11] Patent Number: 5,116,372
[45] Date of Patent: May 26, 1992

[54] ARTIFICIAL LIGAMENT IN SYNTHETIC MATERIALS IMPREGNATED AND COATED WITH ELASTIC RESIN AND ITS COATING PROCEDURE

[76] Inventor: Jacques-Philippe Laboureau, 24, rue de la Fontaine Billenois, 21000 Dijon, France

[21] Appl. No.: 762,734

[22] Filed: Sep. 17, 1991

Related U.S. Application Data

[63] Continuation of Ser. No. 319,813, Mar. 6, 1989, abandoned, which is a continuation of Ser. No. 47,782, May 6, 1987, abandoned.

[30] Foreign Application Priority Data

May 7, 1986 [FR] France .................. 86 06656

[51] Int. Cl.$^5$ ................................. A61F 2/08
[52] U.S. Cl. ................................. 623/13
[58] Field of Search .............. 623/11, 12, 13, 16, 623/18, 66

[56] References Cited

U.S. PATENT DOCUMENTS

| | | | |
|---|---|---|---|
| 3,797,047 | 3/1974 | Pillet et al. | 623/13 |
| 3,973,277 | 8/1976 | Semple et al. | 623/13 |
| 3,987,497 | 10/1976 | Stoy et al. | 623/13 |
| 4,187,558 | 2/1980 | Dahlen et al. | 623/13 |
| 4,455,690 | 6/1984 | Homsy | 623/13 |
| 4,585,458 | 4/1986 | Kurland | 623/13 |
| 4,713,075 | 12/1987 | Kurland | 623/13 |

FOREIGN PATENT DOCUMENTS 1602834 11/1981 United Kingdom .................. 623/13

*Primary Examiner*—David Isabella

[57] ABSTRACT

This inventions concerns a prosthetic ligament which consists of a core (1) constituted from adjacent longitudinal synthetic fibres, which are coated with a biocompatible visco-elastic substance, such as a biocompatible elastomer resin, in the inter-articulate part of the ligament, in such a way as to leave free and uncoated the parts at the opposite extremities of the core.

In order to improve the mechanical qualities of the ligament and make them resemble as closely as possible those of a biological ligament, the fibres of the core are inter-twined before coating with resin and kept inter-twined by this coating.

7 Claims, 2 Drawing Sheets

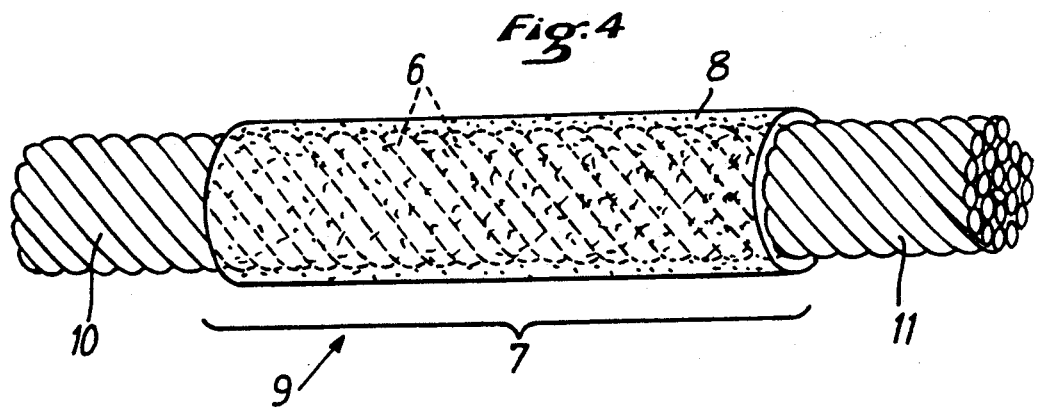
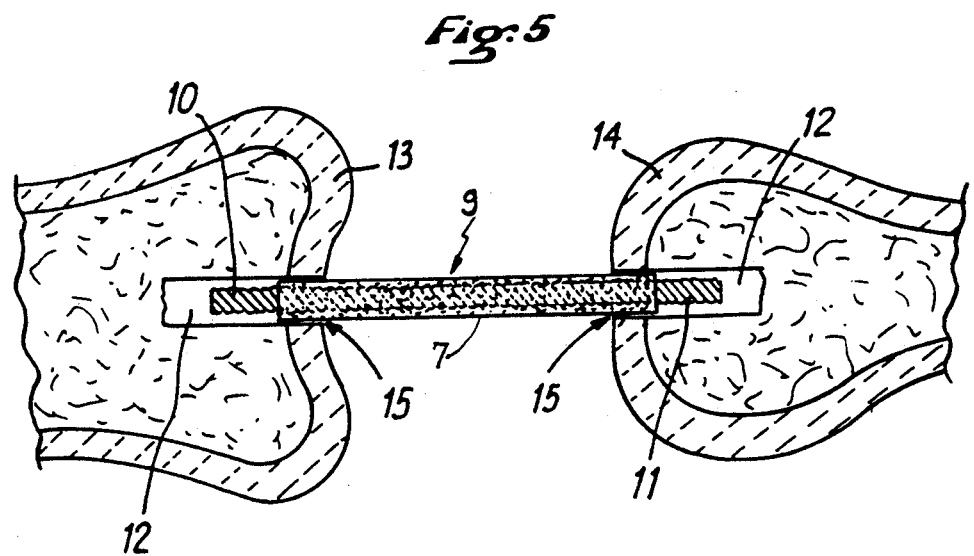
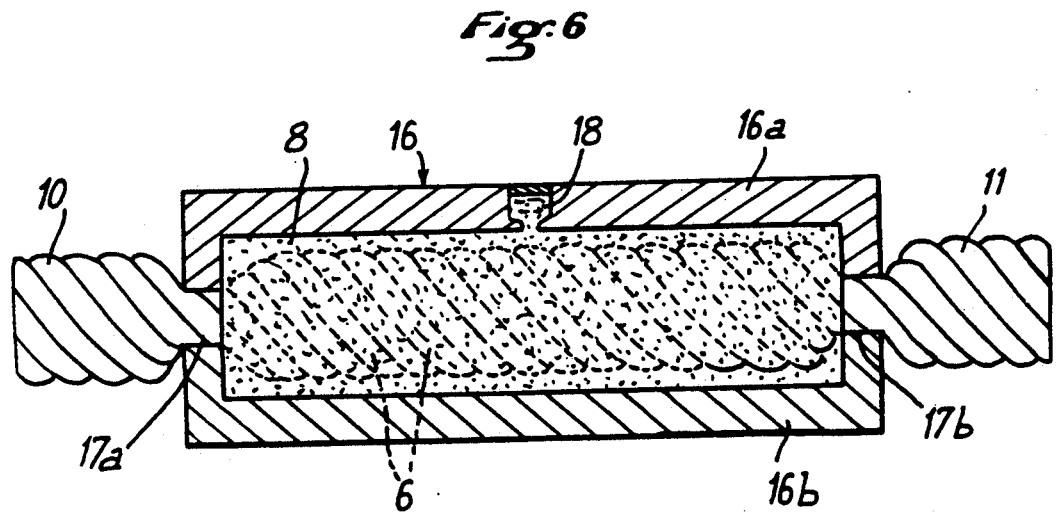

ARTIFICIAL LIGAMENT IN SYNTHETIC MATERIALS IMPREGNATED AND COATED WITH ELASTIC RESIN AND ITS COATING PROCEDURE

This application is a continuation of application Ser. No. 07/319,813, filed Mar. 6, 1989, now abandoned, which is a continuation of application Ser. No. 07/047,782, filed May 6, 1987, now abandoned.

BACKGROUND OF THE INVENTION

This invention concerns an artificial ligament in synthetic material coated with elastic resin as well as the procedure for manufacture of this ligament.

Articular accidents are well-known, notably amongst sporting people, such as tearing or rupture of a ligament; it is also known that in such cases, some of the damaged ligaments cannot reconstitute themselves.

The present-day recognised solution consists of the replacement of the fractured ligament by a prosthetic ligament inserted by classical surgical methods.

In this type of operation, prosthetic ligaments manufactured from synthetic fibres are most frequently used. These fibres are arranged longitudinally to constitute a resistant core of a tube of synthetic textile ensuring the mechanical holding of the whole.

With a suitable length and diameter in relation to the damaged ligament which they are designed to replace, the tube of textile fibres thus constituted undeniably demonstrates a satisfactory mechanical resistance under traction.

However, it can be observed that a piling up of the fibres arranged longitudinally, if it were to satisfy, in the desired proportions, the constraints of traction which in first class ligament implant requires, cannot on the other hand bear any traction overload without risk of permanent deformity. It is well understood in fact that subsequent to an unusual effort of traction, even momentary, on an artificial ligament of the type previously described, the longitudinally placed fibres undergo a relative axial displacement, which nothing can reasonably prevent, the fibres being able to slide one against the other. The risk of establishing an irreversible deformation of the artificial ligament is therefore great.

All the above can be summarised by saying that the artificial ligaments currently available, even if they give good guarantees of resistance to the normal efforts of articulation common to such prostheses, have only a very mediocre capacity to withstand any violent constraint, even passing and accidental.

Moreover, it can frequently be observed that an implantation of an artificial ligament is rejected by the patient's body and undesirable reactions are often to be feared because they are the result of direct contact of the artificial fibres with the biological environment.

Some previous versions are already known, such as the solution described in the patent, FR-A-2135825, in which the manufacture of a tendon from a snap-proof band of knitted polyester fibre arranged at the interior of an independent sheath in elastomer band is proposed. This version produces the characteristic of longitudinal inextensibility and ensures improved smooth running of the band within its elastomer sheath, which is, in principal, the desired function for a tendon which links a muscle to a bone.

Similarly known is, the subordinate solution proposed by the patent, U.S. Pat. No. 3,545,008, which recommends coating the tendons and artificial ligaments with a biocompatible elastomer resin, in such a manner as to isolate the central core from the biological environment and avoid any rejection; as in the previously mentioned french patent, coating the artificial tendon with an elastomer resin furthermore facilitates the smooth running of the tendon in its specific movements.

The patent, EP-A-0051945 is also known in which a particular method of manufacture or a tendon or prosthetic ligament using elastomers is described, as much for the mechanical holding between the fibres, procuring various conformations of the prosthesis in the manner of its applications, as for assuring biocompatibility of the aforesaid implanted prosthesis.

In all these previous versions using a combination of knitted textiles, coated with elastomer, no mention is made of the problem of longitudinal deformations of ligaments undergoing a momentary effort which may, furthermore, be violent in the case of people involved in competitive sports for example.

In conclusion, it is known that a biological ligament can undergo an extension of 30 percent before rupture corresponding to an effort of around 2,000 Newtons and that in general it gives the individual a reserve of reversible extensibility, during a sustained effort corresponding to 1,000 Newtons, of about 18 percent without any damage caused to the aforesaid ligament.

SUMMARY OF THE INVENTION

According to the invention, a new combination of knitted material and elastomer resin has been researched giving the prosthetic ligament mechanical properties close to those of the biological ligament which it is destined to replace.

To this effect, this prosthetic ligament consisting of a core constituted from adjacent longitudinal synthetic fibres, which are coated with a visco-elastic substance, such as bio-compatible elastomer resin, in the inter-articular part of the ligament, in such a way as to leave free and uncoated the opposite extremities of the fibres of the core, is characterised by the fact that the fibres of the core are inter-twined before coating with resin and kept inter-twined by this coating.

According to a complementary characteristic of the invention, before coating the central part of the core, the adjacent synthetic fibres are held firmly one against the other at least up to the extremities of the core, by a column of transversal mesh stitching constituting a support of the chain mesh type of knitting.

According to another complementary characteristic of the invention, the coating of the inter-twined inter-articular part of the core maintained for impregnation at the fusion temperature of visco-elastic, produces, on the one hand, the effect of completely reversible longitudinal elasticity during the constraints normally acceptable to a biological ligament, and on the other hand, a maximum power of elongation before rupture in the region of 30 percent close to the characteristics of a biological ligament.

Preferably, the central coating zone of the inter-twined fibres should extend at least along the whole length of the ligament corresponding to its inter-articular part. This contributes to a great degree to avoidance of phenomena of rejection when the ligament is implanted in the patient, by avoiding direct contact of the textile material with the inter-articular environment, which is known to be responsible for the rejection of prostheses. Of course, the resin used for this coating must be treated, by the methods and procedures which are normal in this field of expertise, to render it biocompatible.

The extremities of the prosthetic ligament, destined to rest within the bone to procure fixation of the aforesaid ligament, are by contrast free of resin coating, the elasticity, qualities of lubrication and the surface condition of which are incompatible with biological assimilation within the inter-bone tunnel.

The extremities of the ligament are, in this manner, fixed by any normal mechanical method, such as surgical staples, procuring for the aforesaid ligament an initial artificial fixation. Thus set in the bone, the extremities of the ligament are assimilated by the same bone which, progressively, imprisons the aforesaid extremities, the surfaces of which demonstrate advantageously all the anfractuosities of the knitting of the textile core of the ligament, thus procuring definitive fixation of the aforesaid ligament in the bone.

BRIEF DESCRIPTION OF THE DRAWINGS

Below is described, by way of a non-limiting example, a method of carrying out the invention, with reference to the attached diagram in which:

FIG. 4 is a perspective view of the prosthetic ligament after impregnation and hardening with the elastomer resin.

FIG. 5 shows an example of the implantation between two bones of a prosthetic ligament according to the invention.

FIG. 6 is an axial cross-section view of a device for moulding and impregnation of elastomer resin on the inter-articular part of the intertwined core in order to form the prosthetic ligament according to the invention.

DETAILED DESCRIPTION OF THE PREFERRED EMBODIMENTS

Figure 1:
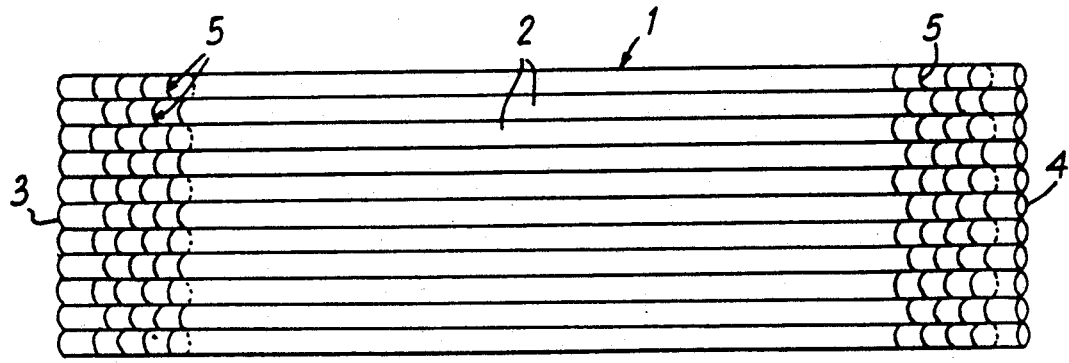
FIG. 1 is a two dimensional surface view of the core destined to become part of the prosthetic ligament according to the invention.

If you refer to FIG. 1, it can be seen that the prosthetic ligament according to the invention is manufactured from a core 1 formed by rectilinear adjacent fibres 2 arranged longitudinally between the two extremities 3 and 4 of the core 1. These fibres 2 are preferably made from a synthetic material such as polyester, the extension capacity properties of which are known to be in the region of 10 to 15 percent. The fibres 3 are held transversally in any appropriate manner, for example by a column of transversal mesh 5 giving them a support of the chain mesh knit type, as shown in FIG. 1. The fibres 3 may be supported along the whole length of the core or only at the two extreme opposite ends of the core.

The knitting thus constituted excludes the possibility of any longitudinal deformation of the unit of rectilinear fibres 2/transversal meshes 5, which could induce an irreversible deformation prejudicial to the core of the ligament. In such a way, that only extension natural to the rectilinear fibres 2 remains possible which moreover becomes irreversible above a certain level of constraint. Finally, the mechanical characteristics of the rectilinear fibres 2 are not affected in any way by their method of solidarisation.

Figure 2:
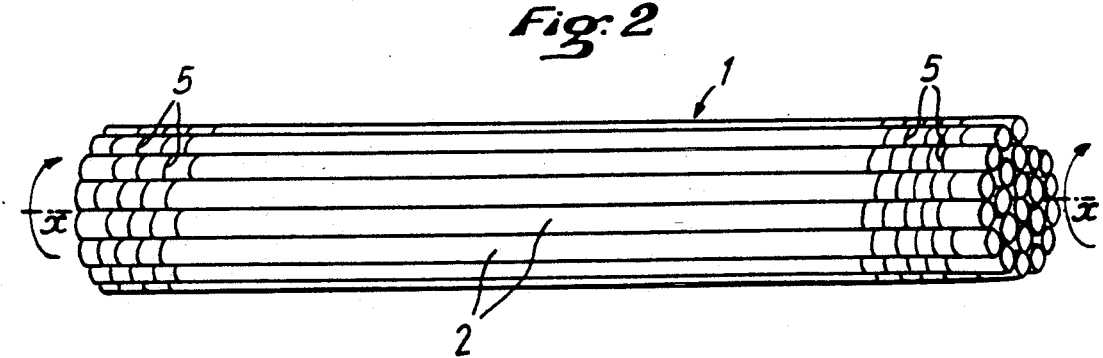
FIG. 2 is a perspective view of the core after being coiled up in on itself around a longitudinal axis.

The core thus obtained is coiled in on itself, as shown in FIG. 2, around its longitudinal axis xx' in three or four concentric joined turns, in such a way as to form a final cylinder, in cross section approximately spiral, with an external diameter roughly approximating that of the biological ligament which it is designed to replace.

Figure 3:
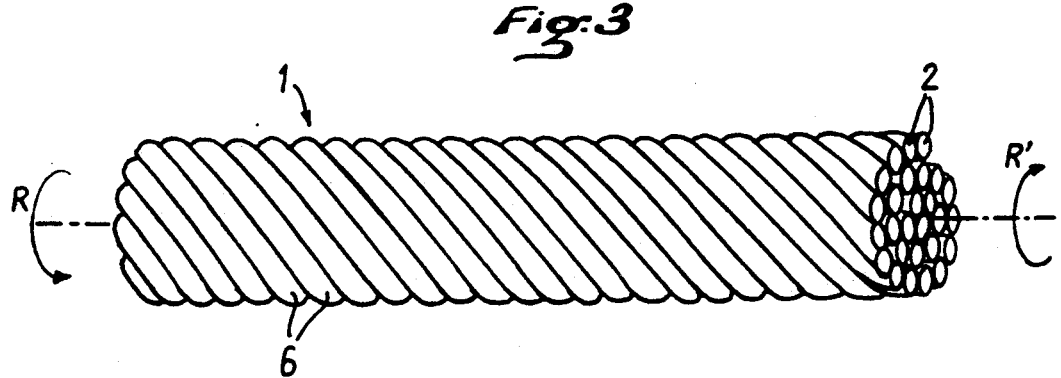
FIG. 3 is a perspective view of the intertwined core before impregnation and coating with resin.

Afterwards, by opposite rotations around the longitudinal axis xx', in the direction of the arrows R and R' (FIG. 3), the extremities 3 and 4 of the core 1 coiled in on itself, the twists 6 are formed, constituted from individual fibres 2 coiled in adjacent spirals. These twists extend along the whole length of the core of the ligament which is thus shortened because of its torsion. The number of spirals of the twists 6 determines, by uniformity of length or by the turns of the individual spirals constituted by the fibres 2, the elasticity of the final prosthetic ligament, this elasticity depends on the desired application.

The core thus spiralled and intertwined is afterwards impregnated and coated, in its single central part 7, designed to constitute the inter-articular part of the ligament, by means of an elastomer resin 8, (FIG. 4), for example of the polyurethane type, at a temperature approximately equal to the fusion point of the resin 8. A prosthetic ligament is thus obtained according to the invention in which the coating 8 of polyurethane ensures the holding of the twists 6 along the entire length of the central or inter-articular zone 7, the two intertwined extremities 10 and 11 of the core 1, which are not impregnated with resin, remain visible, on either side of the central zone 7 impregnated with resin 8. Under these conditions, it is understood that an effort of longitudinal traction between the two extremities 10 and 11 of the ligament 9 causes, by precedence, the coated twists 6 which tend to stretch themselves, to realign. Reciprocally, as soon as the effort ceases, these twists 6 which tend to stretch themselves are realigned by the effect of constraint due to impregnation with elastomer resin 8. Moreover, at the moment of impregnation and coating with the resin 8 at the fusion temperature of this resin, the fibres 2, thus spiralled, of the core 1 of the ligament undergo a thermal retraction, which increases, in the known manner, the power of elongation. In fact the fibres, thus thermally restrained, demonstrate a first rate ability to retract to their original position after extension, in addition to the natural powers of extension under traction of the untreated fibre. Thus it can be observed starting from a non-thermally treated fibre the natural extensibility of which, under a given rate of traction, is for example about 15 percent, a complementary elongation of 15 percent can be obtained by thermal retraction, which endows the treated fibre with a maximum power of elongation close to 30 percent.

By definition, the prosthetic ligament 9 according to the invention demonstrates, on the one hand an optimal power of elongation close to the elongation before rupture of a biological ligament and, on the other hand, an elasticity which results from the addition of two factors, i.e. firstly the elasticity of the central intertwined and coated zone 6 and secondly the natural elasticity of the fibres 2, which can be summarised as follows:.

For longitudinal traction consisting of between 80 and 140 Newtons applied between the two extremities 10 and 11 of the ligament 9, only the intertwined area 7 of the aforesaid ligament absorbs the effort by procuring an average extension of about 12 percent of the ligament 9; this extension is totally reversible due to the elasticity of the elastomer resin 8 as soon as the effort of traction ceases.

For traction of about 1,000 Newtons which corresponds to a violent effort, common amongst sporting people, and which may be repeated, the prosthetic ligament 9 must then have recourse to a reserve of elasticity particular to the fibres 2 in the range of about 6 for normally applicable constraints, endowing the prosthetic ligament 9 with a global elasticity in the range of 18 percent sufficient to encompass such an effort.

For a traction approximating 2,000 Newtons, the prosthetic ligament 9 reaches its rupture limit at exactly the same point as a biological ligament.

By definition, the intertwined prosthetic ligament 9 according to the invention, having qualities of elastic response very close to the biological ligament, procures the advantage of a double return mechanism dealing with normal frequent and daily demands and microtraumas by the inter-play of its twisted zone 7 thus sparing the work of the fibres 2 and consequently increasing the duration of their life.

According to a complementary characteristic of the prosthetic ligament 9, the central zone of the ligament is designed to be coated with resin along the upper length of its inter-articular part in such a way that the extremities of the central zone 7 coated with resin penetrate some way into the inter-bone tunnels 12 drilled in two bones in relation to one another, as can best be seen in FIG. 5. This arrangement prevents any shearing of the fibres 2 constituting the core of the ligament by the edges 15 of the tunnels 12.

The coating of the intertwined ligament 9 according to the invention may be advantageously manufactured by means of a mould 16 consisting of two half shells, 16a and 16b, each one forming a demi-cylindrical internal cavity with a radius slightly greater than that of the intertwined prosthetic ligament and with a length slightly greater than the inter-articular part of the same ligament to be implanted. At each extremity of the two half shells 16a, 16b, an orifice 17a, 17b, with a diameter slightly less than that of the prosthetic ligament, enables the extremities 10, 1 of the core, which should not be coated with resin, to be left outside the mould. Finally, by means of an injector 18, the silicon based elastomer resin, for example polyurethane, is introduced into the mould in at least a half-shell 16a. The latter, being in the form of a paste or molten plaque, spreads out within the mould in a uniform manner and, after polymerisation, endows the intertwined ligament 9, with its exceptional qualities of elasticity on the one hand, and its capacity to be tolerated by the organism, on the other hand.

I claim:

1. A prosthetic ligament, comprising:
   a cylindrical bundle of longitudinally extending and substantially parallel synthetic fibers, said fibers being spirally twisted along the cylindrical axis of the bundle to form a spiral core, the synthetic fibers exhibiting an elastic extension and then a post-elastic deformation to rupture when loaded in traction, the core having a central inter-articular portion and opposite terminal ends; and
   a non-degradable coating of a biocompatible elastomer resin coating only the central inter-articular portion of the core and leaving the terminal ends uncoated, whereby the coating constrains the fibers of the core in its spiral configuration and restores the fibers back to the spiral arrangement upon removal of a tensile load such that when the ligament is subjected to a tensile load the spiral core deforms first elastically by unwinding of the spiral and deforms further by elastic elongation of the fibers.

2. The ligament of claim 1, further including a transverse mesh interconnecting said fibers to each other at each terminal end of said core.

3. The ligament of claim 1, wherein said elastomer resin is a polyurethane resin.

4. A prosthetic ligament, comprising:
   means for supporting a load, the means for supporting including a core made of a bundle of substantially parallel fibers that is spirally twisted about an axis of the bundle to form the core, the fibers being made from a material that exhibits an elastic extension and non-elastic extension when loaded in tension, the fibers being interconnected to each other at their ends by a transverse mesh, the core having a central inter-articular portion and;
   a non-degradable coating of a biocompatible elastomer resin coating only the central inter-articular portion of the core and leaving the terminal ends uncoated, whereby the coating constrains the fibers of the core in its spiral configuration and restores the fibers back to the spiral arrangement upon removal of a tensile load such that when the ligament is subjected to a tensile load the spiral core deforms first elastically by unwinding of the spiral and deforms further by elastic elongation of the fibers, up to about 30 percent before breaking.

5. The ligament of claim 4, wherein said elastomer resin is a polyurethane resin.

6. The ligament of claim 1, further including a transverse mesh comprising a support interconnecting said fibers at at least each terminal end of said core.

7. The ligament of claim 6, wherein the support comprises a warp knitting with weft insertion.

* * * * *